United States Patent
Kasai et al.

(10) Patent No.: US 11,407,772 B2
(45) Date of Patent: Aug. 9, 2022

(54) OPTICALLY-ACTIVE CYCLOPENTENONE DERIVATIVES

(71) Applicants: Tohoku University, Miyagi (JP); Genesis Research Institute, Inc., Aichi (JP); Ouchi Shinko Chemical Industrial Co., Ltd., Tokyo (JP)

(72) Inventors: Hitoshi Kasai, Miyagi (JP); Yoshitaka Koseki, Miyagi (JP); Takaaki Kamishima, Aichi (JP); Shigenobu Aoyagi, Tokyo (JP)

(73) Assignees: Tohoku University, Miyagi (JP); Genesis Research Institute, Inc., Aichi (JP); Ouchi Shinko Chemical Industrial Co., Ltd., Tokyo (JP)

( * ) Notice: Subject to any disclaimer, the term of this patent is extended or adjusted under 35 U.S.C. 154(b) by 0 days.

(21) Appl. No.: 17/269,762

(22) PCT Filed: Sep. 13, 2019

(86) PCT No.: PCT/JP2019/036015
§ 371 (c)(1),
(2) Date: Feb. 19, 2021

(87) PCT Pub. No.: WO2020/059646
PCT Pub. Date: Mar. 26, 2020

(65) Prior Publication Data
US 2021/0300953 A1  Sep. 30, 2021

(30) Foreign Application Priority Data
Sep. 18, 2018  (JP) .............................. JP2018-173190

(51) Int. Cl.
*C07F 7/18* (2006.01)
*C07B 51/00* (2006.01)
*C07B 63/02* (2006.01)
*C12P 7/38* (2006.01)

(52) U.S. Cl.
CPC .............. *C07F 7/188* (2013.01); *C07B 51/00* (2013.01); *C07B 63/02* (2013.01); *C12P 7/38* (2013.01); *C07B 2200/07* (2013.01)

(58) Field of Classification Search
CPC ....... C07C 35/06; C07C 49/537; C07F 7/188; C07B 51/00; C07B 63/02; C07B 2200/07; C12P 7/38
See application file for complete search history.

(56) References Cited

U.S. PATENT DOCUMENTS

| | | | | |
|---|---|---|---|---|
| 11,014,865 B2 * | 5/2021 | Koseki | ................... | C07C 49/537 |
| 2009/0270431 A1 * | 10/2009 | Chu | ................... | C07D 487/04 |
| | | | | 514/265.1 |
| 2021/0024444 A1 * | 1/2021 | Koseki | ................... | C07C 49/537 |

FOREIGN PATENT DOCUMENTS

| | | | |
|---|---|---|---|
| JP | 02000128 A | | 1/1990 |
| JP | 5-271174 A | | 10/1993 |
| WO | 2010/104344 A1 | | 9/2010 |
| WO | 2018/220888 A1 | | 12/2018 |

OTHER PUBLICATIONS

N. Nazef et al., 14 Organic Letters (2012) (Year: 2012).*
T. Kamishima et al., 60 Tetrahedron Letters (Apr. 16, 2019) (Year: 2019).*
T.W. Greene, Greene's Protective Groups in Organic Synthesis, Chapters 2 and 4 (4th ed., 2007) (Year: 2007).*
Y. Kojima et al., 96 the Journal of Bioscience and Bioengineering, 219-226 (2003) (Year: 2003).*
C. Chen et al., 82 Journal of the Science of Food and Agriculture, 601-605 (2002) (Year: 2002).*
T. Kamishima et al., 91 Bull. Chem. Soc. Jpn., 1691-1696 (2018) (Year: 2018).*
M. Barros et al., 36 Tetrahedron Letters, 2321-2324 (1995) (Year: 1995).*
S. Achab et al., J. Chem. Soc. Perkin Trans. 1, 2863-2873 (1990) (Year: 1990).*
E. Ruediger et al., 45 Tetrahedron Letters, 739-742 (2004) (Year: 2004).*
S. Achab et al., J. Chem. Soc., Chem Commun., 1040-1041 (1984) (Year: 1984).*
M. Barros et al., 35 Tetrahedron Letters, 3999-4002 (1994) (Year: 1994).*
G. Moss et al., 67 Pure and Applied Chemistry (De Gruyter, 1995) (Year: 1995).*
IUPAC. Compendium of Chemical Terminology, 2nd ed., Compiled by A. D. McNaught and A. Wilkinson. Blackwell Scientific Publications, Oxford (1997) (Year: 1997).*
Barros, M. Teresa et al., "On the diastereoselectivity of the 1, 2-reduction of 2-alkyl-4-hydroxycyclopentenones with sodium borohydride in the presence of cerium (III): Synthesis of prostaglandin precursors", Tetrahedron Letters, 1995, vol. 36, No. 13, pp. 2321-2324.
International Search Report and Written Opinion, PCT/JP2019/036015, Japan Patent Office, dated Nov. 26, 2019.
Kluge, AF et al., "Prostaglandins. XI. Synthesis of 13-cis-prostaglandins via a highly stereoselective conjugate addition with a functionalized organocopper reagent", J. Am. Chem. Soc., 1972, 94, 26, 9256.

(Continued)

*Primary Examiner* — Alexander R Pagano
(74) *Attorney, Agent, or Firm* — Gavrilovich, Dodd & Lindsey LLP

(57) ABSTRACT

The present invention provides: industrially desirable and novel optically-active cyclopentenone derivatives; and a novel industrial manufacturing method. The novel optically-active cyclopentenone derivatives and method for manufacturing the same are, respectively: an intermediate for industrially desirable and novel prostaglandin derivatives and the like; and a method for manufacturing the same. It is expected that the present invention will be commercialized and industrialized.

5 Claims, No Drawings

(56) References Cited

OTHER PUBLICATIONS

Okamoto, Sentaro et al., "Prostaglandin synthesis via two-component coupling. Highly efficient synthesis of chiral prostaglandin intermediates 4-alkoxy-2-alkyl-2-cyclopenten-1-one and 4-alkoxy-3-alkenyl-2-methylenecyclopentan-1-one", J. Org. Chem., 1988, 53, 23, 5590-5592.

Ruediger, Edward et al., "Novel 3'—deoxy analogs of the anti-HBV agent entecavir: synthesis of enantiomers from a single chiral epoxide", Tetrahedron Letters, 2004, vol. 45, pp. 739-742.

Suzuki, M. et al., "Prostaglandin synthesis. 16. The three-component coupling synthesis of prostaglandins", J. Am. Chem. Soc., 1988, 110, 14, 4178-4126.

\* cited by examiner

OPTICALLY-ACTIVE CYCLOPENTENONE DERIVATIVES

CROSS REFERENCE TO RELATED APPLICATIONS

This application is a U.S. National Phase Application filed under 35 U.S.C. § 371 and claims priority to International Application No. PCT/JP2019/036015, filed Sep. 13, 2019, which application claims priority to Japanese Application No. 2018-173190, filed Sep. 18, 2018, the disclosures of which are incorporated herein by reference.

TECHNICAL FIELD

The present invention relates to optically-active cyclopentenone derivatives and a method for manufacturing the same.

BACKGROUND ART

Prostaglandin $E_1$ (abbreviated as $PGE_1$ hereinafter) has characteristic effects, such as platelet aggregation inhibitory and blood pressure lowering. It has already been put into practical use as a medicine for improving peripheral circulation disorder. Thus, a large number of $PGE_1$ analogs have also been studied.

In order to manufacture $PGE_1$ and derivatives thereof, several methods have been developed so far, such as Corey lactone method (patent document 1), a method using conjugated addition reaction (non-patent document 1), ligation of three components (non-patent document 2), and ligation of two components (non-patent document 3 and patent document 2). However, these methods have problems of having too many steps and poor efficiency.

The 4-hydroxy-2-hydroxymethyl-2-cyclopentenone derivatives can be production intermediates of $PGE_1$ and its derivatives as well as other pharmacologically-active substances. However, it is chemically very difficult to selectively protect the equivalent aryl alcohol form in the skeleton of cyclopentenone. Technique of methods with good efficiency has not yet been established. Furthermore, it is desirable to develop a method for efficiently manufacturing optically-active 4-hydroxy-2-hydroxymethyl-2-cyclopentenone derivatives.

PRIOR ART LITERATURE

Patent Documents

1. WO2010/104344
2. Japanese Patent Publication No. Heisei 2-128

Non-Patent Documents

1. J. Am. Chem. Soc., 1972, 94, 9256
2. J. Am. Chem. Soc., 1988, 110, 4718-4126
3. J. Org. Chem., 1988, 53, 5590

SUMMARY OF THE INVENTION

Problems to be Solved by the Invention

The objective of the invention is to overcome the disadvantage and to solve the problems in prior art as described above, and to provide a compound represented by formula (I) or an optically-active form thereof, and a method for manufacturing the same.

Means for Solving the Problems

In view of the above situation, the present inventors have studied diligently the cyclopentenone derivatives usable as synthetic intermediates for $PGE_1$ and derivatives thereof and a method for manufacturing the same. As a result, the present inventors have succeeded in manufacturing 4-hydroxy-2-hydroxymethyl-2-cyclopentenone (the compound represented by formula (1)) by hydrothermal reaction from monosaccharide. The present inventors have found out that the optically-active forms of (3) and (4) can be manufactured at once the by using 4-hydroxy-2-hydroxymethyl-2-cyclopentenone as a starting material, protecting only a primary alcohol position-selectively, and then reacting the protected compound (2) with a carboxylic acid ester of an unsaturated alcohol in the presence of a hydrolase. The present inventors have completed the present invention on the basis of this finding.

In other words, the present invention has solved the above problems by providing the inventions described in the following [1] to [11].

[1] A compound represented by formula (I) or an optically-active form thereof,

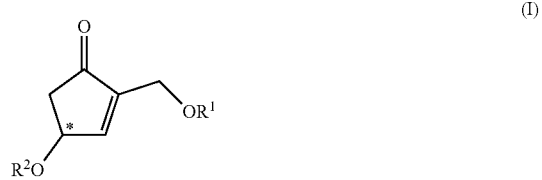

(I)

wherein, $R^1$ is silyl group represented by formula (i), alkyl group, aryl group, arylalkyl group, or a group that forms an acetal bond together with the oxygen atom of hydroxyl group. $R^2$ is hydrogen atom or acyl group. The mark * represents an asymmetric carbon atom.

(i)

wherein, $R^3$, $R^4$ and $R^5$ are alkyl group which may have a substituent, aryl group which may have a substituent, and arylalkyl group which may have a substituent, respectively.

[2] A compound or an optically-active form thereof according to [1], wherein the $R^1$ is silyl group represented by formula (i) (wherein, the $R^3$, $R^4$ and $R^5$ are as defined by [1]) or arylalkyl group.

[3] A compound or an optically-active form thereof according to [1] or [2], wherein the $R^3$, $R^4$ and $R^5$ are $C_1$-$C_6$ alkyl group which may have a substituent, $C_6$-$C_{10}$ aryl group which may have a substituent, and $C_7$-$C_{14}$ arylalkyl group which may have a substituent, respectively.

[4] A compound or an optically-active form thereof according to any one of [1] to [3], wherein the $R^3$, $R^4$ and $R^5$ are each $C_1$-$C_6$ alkyl group which may have a substituent.

[5] A compound or an optically-active form thereof according to [1] or [2], wherein the arylalkyl group is $C_7$-$C_{20}$ arylalkyl group.

[6] A compound or an optically-active form thereof according to [1], wherein the $R^1$ is silyl group represented by formula (i) or arylalkyl group, and the $R^2$ is hydrogen atom.

[7] A compound or an optically-active form thereof according to [1], wherein the $R^1$ is a silyl group represented by formula (i) or arylalkyl group, and the $R^2$ is acyl group.

[8] A method for manufacturing the compound of formula (2) (wherein, the $R^1$ is as defined by [1]) or an optically-active form thereof, characterized in that the compound of formula (1) is reacted with a silyl halide or an arylalkyl halide in the presence of a base.

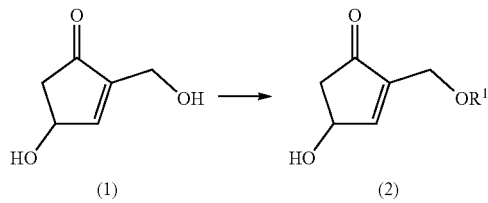

[9] A method wherein the compound of formula (2) and a carboxylic acid ester of an unsaturated alcohol are reacted in the presence of a hydrolase to give a mixture of the compounds of formula (3) and formula (4) (wherein, the $R^1$ is as defined by [1], and the $R^2$ is acyl group), which is then separated to manufacture the optically-active cyclopentenone of formula (3) and formula (4).

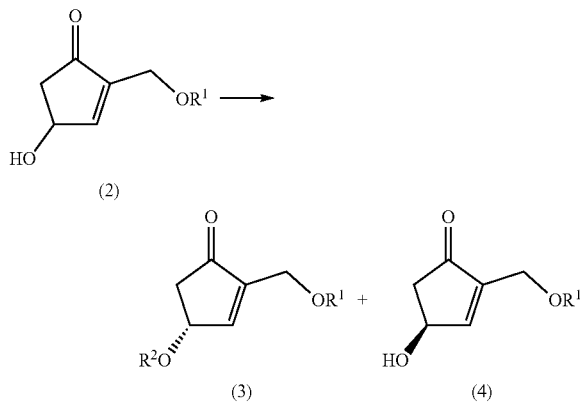

[10] A method according to [9], wherein the carboxylic acid ester of an unsaturated alcohol is vinyl acetate, vinyl propionate, vinyl valerate, isopropenyl acetate, isopropenyl propionate, or isopropenyl valerate, and the hydrolase is lipase.

[11] A method according to [9], wherein the carboxylic acid ester of an unsaturated alcohol is vinyl acetate, and the hydrolase is Lipase PS (Amano) or Lipase AK (Amano).

Effects of the Invention

A compound represented by formula (I), an optically-active form thereof, and a novel industrial method for manufacturing the same are provided by the present invention.

According to the method of the present invention, among the two hydroxyl groups of 4-hydroxy-2-hydroxymethyl-2-cyclopentenone, only one of them can be selectively protected. The targeted compound (I) is easily obtained.

Besides, in the method of the present invention, the compound (1) is used to react with carboxylic acid ester of an unsaturated alcohol in the presence of a hydrolase, whereby the targeted optically-active form of the compound (I) is easily obtained.

In the method of the present invention, by using the compound (1), the targeted $PGE_1$ or its derivatives can be manufactured easily and efficiently with high yields on industrial scales.

Furthermore, a compound represented by formula (I) or optically-active forms thereof, which are useful as medicines and intermediates thereof can be provided according to the method of the present invention. The novel compounds obtained by the method of the present invention are expected to be useful as intermediates and reagents of medicines such as $PGE_1$.

EMBODIMENTS FOR CARRYING OUT THE INVENTION

The present invention will be described in detail below. The terms used in the specification are described below. Unless otherwise stated, the terms used in the specification and claims have the meanings set forth below.

Unless specifically limited, an "alkyl group" refers to a saturated aliphatic hydrocarbon group, for example, a linear or branched alkyl group with 1-20 carbon atoms. The examples include $C_1$-$C_6$ alkyl groups, such as methyl group, ethyl group, propyl group, isopropyl group, butyl group, sec-butyl group, isobutyl group, pentyl group, hexyl group or the like, heptyl group, 1-methylhexyl group, 5-methylhexyl group, 1,1-dimethylpentyl group, 2,2-dimethylpentyl group, 4,4-dimethylpentyl group, 1-ethylpentyl group, 2-ethylpentyl group, 1,1,3-trimethylbutyl group, 1,2,2-trimethylbutyl group, 1,3,3-trimethylbutyl group, 2,2,3-trimethylbutyl group, 2,3,3-trimethylbutyl group, 1-propylbutyl group, 1,1,2,2-tetramethylpropyl group, octyl group, 1-methylheptyl group, 3-methylheptyl group, 6-methylheptyl group, 2-ethylhexyl group, 5,5-dimethylhexyl group, 2,4,4-trimethylpentyl group, 1-ethyl-1-methylpentyl group, nonyl group, 1-methyloctyl group, 2-methyloctyl group, 3-methyloctyl group, 7-methyloctyl group, 1-ethylheptyl group, 1,1-dimethylheptyl group, 6,6-dimethylheptyl group, decyl group, 1-methylnonyl group, 2-methylnonyl group, 6-methylnonyl group, 1-ethyloctyl group, 1-propylheptyl group, n-nonyl group, n-desyl group, etc. However, a $C_1$-$C_6$ alkyl group is preferable. Preferable examples of the $C_1$-$C_6$ alkyl group are methyl group, ethyl group, propyl group, isopropyl group, butyl group, sec-butyl group, isobutyl group, pentyl group or hexyl group.

An "aryl group" refers to a monocyclic or bicyclic aromatic hydrocarbon group, preferably a $C_6$-$C_{10}$ aryl group such as phenyl group and naphthyl group, and more preferably phenyl group.

An "arylalkyl group" refers to an alkyl substituted with aryl such as phenyl, naphthyl, anthryl, phenanthryl, acenaphthenyl, and the like. The examples include benzyl, 2-phenylethyl, 3-phenylpropyl, 2-phenylpropyl, 1-phenylpropyl, α-naphthylmethyl, α-naphthylethyl, β-naphthylmethyl, β-naphthylethyl, diphenylmethyl, triphenylmethyl, and the like, among which triphenylmethyl group is preferable.

The term "which may have a substituent" means that a compound may have a substituent or may be unsubstituted. When a compound has a substituent (or substituents), there may be 1-5 substituents, preferably 1-3 substituents on possible positions. In the case where the number of substituents is two or more, each substituent may be the same or different. Examples of substituents include alkyl group, alkoxy group, halogen atom, cyano group, nitro group and the like, preferably $C_1$-$C_6$ alkyl group, $C_1$-$C_6$ alkoxy group or halogen atom.

Examples of the $C_1$-$C_6$ alkyl groups include, but are not limited thereto, methyl group, ethyl group, propyl group, isopropyl group, butyl group, sec-butyl group, isobutyl group, pentyl group or hexyl group and the like.

Examples of the $C_1$-$C_6$ alkoxy groups include, but are not limited thereto, methoxy group, ethoxy group, propoxy group, isopropoxy group, butoxy group, sec-butoxy group, isobutoxy group, tert-butoxy group, pentyloxy group, isopentyloxy group, hexyloxy group, isohexyloxy group and the like.

A "halogen atom" refers to fluorine atom, chlorine atom, bromine atom, iodine atom or the like, preferably fluorine atom and chlorine atom.

Specific examples of the $R^3$, $R^4$ and $R^5$ of a silyl group represented by formula (i) include, but are not limited thereto, methyl group, ethyl group, propyl group, isopropyl group, butyl group, sec-butyl group, tert-butyl group, pentyl group, hexyl group, phenyl group, or a combination thereof, and tert-butyldimethylsilyl, tert-butyldiphenylsilyl and methyldiphenylsilyl, preferably tert-butyldimethylsilyl.

Examples of the group that forms an acetal bond together with the oxygen atom of hydroxyl group include, but are not limited thereto, methoxymethyl, 1 ethoxyethyl, (2-methoxyethoxy) methyl, tetrahydropyranyl group and the like.

Specific examples of acyl groups include, but are not limited thereto, acetyl, propionyl, n-butyryl, iso-butyryl, n-valeryl, caproyl, benzoyl, and the like.

Specific examples of the carboxylic acid ester of an unsaturated alcohol include, but are not limited thereto, vinyl acetate, vinyl propionate, vinyl valerate, isopropenyl acetate, isopropenyl propionate, isopropenyl valerate, and the like.

Specific examples of the hydrolase include, but are not limited thereto, commercially available hydrolase, such as Lipase AK (Amano), Lipase PS (Amano), Lipase PS Amano SD (Amano), Lipase AYS (Amano), Lipase G Amano 50 (Amano), Lipase PSIM (Amano), Lipase F-AP15 (Amano), CHIRAZYME L-6 (Roche), Lipase-OML (Meito), Lipase TL (Meito), Lipase-MY-30 (Meito), Lipase-SL (Meito), Lilipase A-10D (Nagase Chemtex), KM-109 (Nagase Chemtex), Immobilizedlipase (Toyobo), preferably Lipase AK (Amano).

The compounds described herein may contain asymmetric centers, and thus they may have enantiomers. When the compounds described herein have two or more asymmetric centers, they may also be present as diastereomers. Enantiomers and diastereomers are included in a broader class of stereoisomers. It is intended that all possible stereoisomers, such as substantially purely separated enantiomers, racemic mixtures thereof, and mixtures of diastereomers are included. All stereoisomers of the compounds disclosed herein are intended to be included. Unless otherwise stated, reference to an isomer is applied to any possible isomers. Whenever the composition of isomers is not specified, all possible isomers are included.

A Method for Manufacturing Compound (I) of the Invention

Protection of Hydroxyl Group of Compound (1) (Manufacture of Compound (2))

Reactions of silylation and alkylation of the hydroxyl group of compound (1) will be described. The hydroxyl group of compound (1) can be silylated by reacting with a silyl halide in the presence of a base. For example, according to following methods or methods similar to them (e.g., silyl etherification or the like described by Corey, E. J. et al., in J. Am. Chem. Soc., 94, 6190, 1972; and by Morita, T. et al., in Tetrahedron Lett., 21, 835, 1980; as well as by Y. Kita, et al., in Tetrahedron Lett., 4311, 1979. As a review by Lalonde, M., Chan, T. H., in Synthesis, 817-845, 1985, etc.), compound (i) can react with a silyl halide compound. The hydroxyl group of compound (1) can be alkylated by reacting with an alkyl halide in the presence of a base. For example, according to following methods or methods similar to them (e.g., silyl etherification or the like described by S. K. Chaudhary et al., in Tetranderon let., 20, 95, 1979; and by S. Schiltz et al., in J. Organomet. Chem., 691, 5438, 2006), compound (i) can react with a silyl halide compound.

(Silyl Halide)

The type of silyl halide compound is not particularly limited. Any of those used in the art can be used in the method of the present invention. For example, a trialkylsilyl halide compound, a monoalkyl diarylsilyl halide compound, a triarylsilyl halide compound or the like can be used. In case that a silyl halide compound has an alkyl group, as the alkyl group for example, methyl group, ethyl group, n-propyl group, isopropyl group, n-butyl group, sec-butyl group, isobutyl group, or tert-butyl group and the like, preferably methyl group or ethyl group can be used. In case that a silyl halide compound has an aryl group, phenyl group or the like can be used. As the halogen atom consisting the silyl halide compound, chlorine atom, bromine atom, or iodine atom or the like, preferably chlorine atom can be used. More specifically, the examples of silyl halide compounds include trimethylsilylchloride (also referred to as trimethylchlorosilane, and the same applies to the following compounds), triethylsilyl chloride, tert-butyldimethylsilyl chloride, tert-butyldiphenylsilyl chloride, triphenylsilyl chloride, and the like.

(Arylalkyl Halide)

Examples of the arylalkyl halide include benzyl chloride, 2-phenylethylchloride, 3-phenylpropyl chloride, 2-phenylpropyl chloride, 1-phenylpropyl chloride, α-naphthylmethyl chloride, α-naphthylethyl chloride, β-naphthylmethyl chloride, β-naphthylethyl chloride, diphenylmethyl chloride, triphenylmethyl chloride, benzyl bromide, 2-phenylethyl bromide, 3-phenylpropyl bromide, 2-phenylpropyl bromide, 1-phenylpropyl bromide, α-naphthylmethyl bromide, α-naphthylethyl bromide, β-naphthylmethyl bromide, β-naphthylethyl bromide, diphenylmethyl bromide, triphenylmethyl bromide, benzyl iodide, 2-phenylethyl iodide, 3-phenylpropyl iodide, 2-phenylpropyl iodide, 1-phenylpropyl iodide, α-naphthylmethyl iodide, α-naphthylethyl iodide, β-naphthylmethyl iodide, β-naphthylethyl iodide, diphenylmethyl iodide, triphenylmethyl iodide, and the like.

(Base)

Examples of the bases used include organic bases and inorganic bases. Examples of the organic bases include, but are not limited thereto, triethylamine, N,N-diisopropylethylamine, imidazole, pyridine, 4-dimethylaminopyridine (DMAP), n-butyllithium and potassium tert-butoxide, preferably trimethylamine and N,N-diisopropylethylamine. Examples of the inorganic bases include, but are not limited thereto, sodium hydride, sodium carbonate, sodium bicarbonate, potassium carbonate, potassium bicarbonate or cesium carbonate. The amount of the base used is preferably equal to or more than the equivalent of the compound used as raw material. Furthermore, with respect to 1 mol of the compound used as raw material, the range of 1.0-10.0 mol can usually be exemplified, preferably the range of 2.0-6.0 mol, and more preferably the range of 2.0-4.0 mol.

(Solvent)

In view of the smooth progress of reactions, the reaction of the present invention is preferably carried out in the presence of a solvent. The solvent in the reaction of the present invention may be any solvent as long as the reaction proceeds.

Regarding the solvent in the reaction of the present invention, specific and preferable examples include, but are not limited thereto, ethers (such as tetrahydrofuran (THF), diisopropyl ether, dibutyl ether, cyclopentylmethyl ether (CPME), methyl-tert-butyl ether, more preferably tetrahydrofuran (THF)), amides (such as N,N-dimethylformamide (DMF), N,N-dimethylacetamide (DMAC), N,N-diethylacetamide, N-methylpyrrolidone (NMP) and the like, preferably N,N-dimethylformamide (DMF), N,N-dimethylacetamide (DMAC), N-methylpyrrolidone (NMP), and more preferably N,N-dimethylformamide (DMF)), and sulfoxides (such as dimethylsulfoxide (DMSO), and the like). The amount of solvent used may be any amount as long as the reaction proceeds. The amount of solvent used in the reaction of the present invention can be appropriately adjusted by a person skilled in the art.

(Reaction Temperature)

The reaction temperature of the present invention is not particularly limited. In one embodiment, from the viewpoints of improvement in yield, suppression of by-products, and economic efficiency, etc., the ranges of −20° C.-50° C. (i.e., minus 20° C. to plus 50° C.), preferably −10° C.-30° C. (i.e., minus 10° C. to plus 30° C.), and more preferably 0° C.-25° C. can be exemplified.

(Reaction Time)

The reaction time of the present invention is not particularly limited. In one embodiment, from the viewpoints of improvement in yield, suppression of by-products, and economic efficiency, etc., the ranges of 0.5-120 hours, preferably 1-72 hours, more preferably 1-48 hours, and even more preferably 1-24 hours can be exemplified. However, the reaction time of the present invention can be appropriately adjusted by a person skilled in the art.

Regarding the post-treatment of the reaction, general treatment for acquiring products from reaction mixtures may be performed. For example, after completion of the reaction, added water, or hydrochloric acid and the like to the reaction mixture to neutralize, and extract with a general extraction solvent such as ethyl acetate, diethyl ether, methylene chloride, toluene, hexane and the like. An objective can be obtained after removing the reaction solvent and the extraction solvent under reduced pressure from the obtained extract. If necessary, general purification with silica gel chromatography, distillation, recrystallization, or the like may be performed on the objective obtained in this way to furtherly improve its purity.

Acylation of Compound (2)

The acylation of compound (2) will be described. Compound (2) can be acylated by reacting with a carboxylic acid ester of an unsaturated alcohol in the presence of a hydrolase.

(Hydrolase)

Examples of the hydrolase used include, but are not limited thereto, commercially available hydrolase, such as Lipase AK (Amano), Lipase PS (Amano), Lipase PS Amano SD (Amano), Lipase AYS (Amano), Lipase G Amano 50 (Amano), Lipase PSIM (Amano), Lipase F-AP15 (Amano), CHIRAZYME L-6 (Roche), Lipase-OML (Meito), Lipase TL (Meito), Lipase-MY-30 (Meito), Lipase-SL (Meito), Lilipase A-10D (Nagase Chemtex), KM-109 (Nagase Chemtex), Immobilizedlipase (Toyobo), preferably Lipase AK (Amano).

Various forms of the hydrolase can be used, such as those purified, or those adsorbed to diatomaceous earth or the like, as well as those immobilized on bead glass or the like. The amount of the enzyme is usually 0.01-1 time by weight, preferably 0.03-0.5 time by weight, and more preferably 0.05-0.2 time by weight with respect to compound (2).

(Carboxylic Acid Ester of Unsaturated Alcohol)

Examples of the carboxylic acid ester of unsaturated alcohol used include vinyl acetate, vinyl propionate, vinyl valerate, isopropenyl acetate, isopropenyl propionate, isopropenyl valerate, and the like. The amount used is usually 0.5 times or more in mol, and preferably 2 times or more in mol with respect to compound (2). Besides, a carboxylic acid ester of unsaturated alcohol can also be used as a solvent.

(Solvent)

In the reaction, a solvent can be used. Except the above-mentioned carboxylic acid ester of unsaturated alcohol, examples of the solvent include a single solvent or a mixed solvent of aliphatic hydrocarbons (such as hexane, heptane, benzene, toluene, dichloromethane, chloroform, dibutyl ether, and the like), aromatic hydrocarbons, halogenated hydrocarbons, ethers and the like. The amount used is usually 0.5-10 times by weight with respect to compound (2).

(Reaction Temperature and Reaction Time)

The reaction temperature is usually 10-50° C. The reaction time of 0.5-50 hours is usually sufficient. The reaction can be monitored by determining the optical purity of compound (3) or compound (4) using liquid chromatography provided with a filler for optically-active compounds, or the like. In addition, the completion of the reaction can also be determined in this way. Alternatively, use normal liquid chromatography or the like (not especially for use in optically-active compounds) to determine the ratio of an alcohol (compound (2) and/or the optically-active cyclopentenone derivative (compound (4)) to an ester (the optically-active cyclopentenone ester (compound (3)). The completion of reaction can be determined when the ratio is about 1:1. After completion of the reaction, if necessary, by adding a solvent such as aliphatic or aromatic hydrocarbon (for example, hexane, heptane, benzene, toluene, dichloromethane, chloroform, chlorobenzene, dichloroethane, ethyl acetate, ethyl ether, or the like), ether, ketone, ester, halogenated hydrocarbon, etc. to the reaction, filtering the enzyme, and then concentrating the filtrate, a mixture of the optically-active cyclopentenone derivative (compound (4)) and the optically-active cyclopentenone ester (compound (3) can be obtained. Additionally, by subjecting the mixture to a conventional chromatographic treatment, the optically-active cyclopentenone derivative (compound (4)) and the optically-active cyclopentenone ester (compound (3)) can be separated.

EMBODIMENTS

The present invention will be described with examples in more detail below. However, the present invention is not limited to these examples. In this specification, room temperature is referred to 10° C.-35° C. The following equipment is used in the determination of various physical properties in the examples. Yanaco Mp-500V (Anatec Yanaco)

EXAMPLE 1

Manufacture of 4-hydroxy-2-(tert-butyldimethylsilyl) oxymethyl) cyclopenta-2-en-1-one

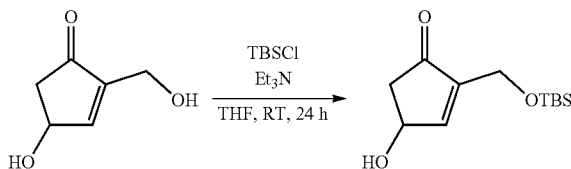 [SMILES: O=C1CC(O)C=C1CO ; CC(C)(C)[Si](C)(C)OCC1=CC(O)CC1=O]

Tert-butyldimethylsilyl chloride (3.29 g, 21.8 mmol) and triethylamine (3.8 mL, 27.3 mmol) were added at room temperature to a THF solution (20 mL) of 4-hydroxy-2-hydroxymethyl) cyclopenta-2-en-1-one (1.4 g, 10.9 mmol). After stirring the reaction solution at the same temperature for 24 hours, an aqueous solution of saturated ammonium chloride was added to stop the reaction. The mixture was separated using ethyl acetate (2×30 mL). The organic layer was washed with saturated brine and dried over anhydrous magnesium sulfate. The residue remaining after removal under reduced pressure was purified by silica gel chromatography (hexane/EtOAc 2:1→1:1). 4-hydroxy-2-(tert-butyldimethylsilyl) oxymethyl) cyclopenta-2-en-1-one (2.17 g, 82%) was obtained as a colorless to pale yellow oily substance.

$^1$H NMR (400 Mz, CDCl$_3$): δ 0.080 (s, 3H), 0.085 (s, 3H), 0.92 (s, 3H), 1.91 (d, J=5.2 Hz), 2.37 (dd, J=2.0, 18.8 Hz, 1H), 2.86 (dd, J=6.0, 18.8 Hz, 1H), 4.37-4.38 (m, 2H), 4.99 (brs, 1H), 7.37-7.38 (m, 1H) ppm; $^{13}$C NMR (100 Mz, CDCl$_3$): δ 5.35, 5.32, 18.4, 26.0 (3C), 45.8, 58.0, 68.9, 148.4, 155.9, 204.8 ppm.

EXAMPLE 2

Manufacture of an Optically-Active Cyclopentenone

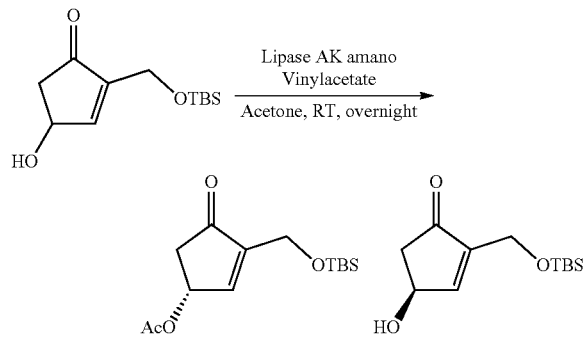

Lipase AK amano (1.1 g) was added to acetone-vinyl acetate solution (26 mL, 1:1) of 4-hydroxy-2-(tert-butyldimethylsilyl) oxymethyl) cyclopenta-2-en-1-one (2.2 g, 9.04 mmol) at room temperature and stirred at the same temperature overnight. After removing the enzyme was by filtration, the filtrate was distilled off under reduced pressure. The residue obtained was purified with silica gel chromatography (hexane/EtOAc 3:1→1:1). 4R-acetoxy-2-(tert-butyldimethylsilyl) oxymethyl) cyclopenta-2-en-1-one ((R)-AC form) (1.25 g, 48%) and 4S-hydroxy-2-(tert-butyldimethylsilyl) oxysilyl) cyclopenta-2-en-1-one ((S)-mono TBS form) (1.1 g, 50%) were obtained, respectively.

(R)-AC form:
$^1$H NMR (400 Mz, CDCl$_3$): δ 0.084 (s, 3H), 0.086 (s, 3H), 0.92 (s, 9H), 2.10 (s, 3H), 2.41 (dd, J=2.0, 18.8 Hz, 1H), 2.91 (dd, J=6.0, 18.2 Hz, 1H), 4.40 (t, J=2.0 Hz, 2H), 5.78-5.82 (m, 2H), 7.36 (q, J=2.4, 1H) ppm; $^{13}$C NMR (100 Mz, CDCl$_3$) δ 5.36, 18.4, 21.1, 26.0 (3C), 42.6, 58.1, 70.5, 150.0, 152.1, 170.7, 203.6 ppm.

Enantiomer excess: 92% ee (Chiral ART (YMC), Cellulose-SC, 250×4.6 mm I.D., hexane/i-propanol=90/10)

(S)-mono TBS form:
$[α]_D^{19}$=−11.6 (c=1.0 in CHCl$_3$)

EXAMPLE 3

Manufacture of 4S-hydroxy-2-(tert-butyldimethylsilyloxymethyl) cyclopenta-2-en-1-one

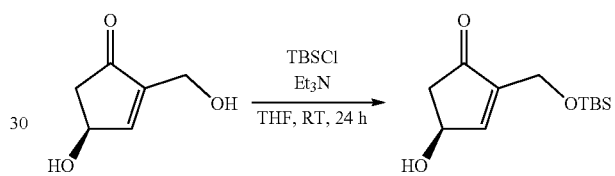

tert-butyldimethylsilyl chloride (405 mg, 2.69 mmol) and triethylamine (0.5 mmol, 3.58 mmol) were added to a THF solution (6 mL) of 4S-hydroxy-2-hydroxymethylcyclopenta-2-en-1-one (230 mg, 1.79 mmol) at room temperature. After stirring the reaction solution at the same temperature for 24 hours, an aqueous solution of saturated ammonium chloride was added to stop the reaction. The mixture was separated using ethyl acetate (2×10 mL). The organic layer is washed with saturated brine and dried over anhydrous magnesium sulfate. The residue remaining after the removal under reduced pressure was purified with silica gel chromatography (hexane/EtOAc 2:1→1:1). 4S-hydroxy-2-(tert-butyldimethylsilyloxymethyl) cyclopenta-2-en-1-one (306 mg, 70%) was obtained as a colorless to pale yellow oily substance. The various spectral data were the same as those in Example 1. Besides, the optical rotation matched well with that in Example 2. $[α]_D^{19}$=−11.8 (c=1.0 in CHCl$_3$)

EXAMPLE 4

Manufacture of 4-hydroxy-2-(triphenylmethyloxymethyl) cyclopenta-2-en-1-one

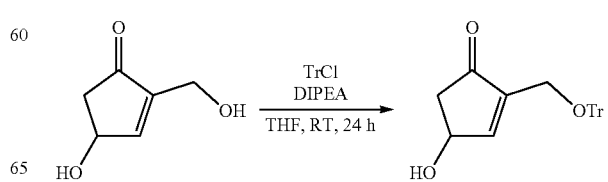

Triphenylmethyl chloride (993 mg, 3.56 mmol) and diisopropylethylamine (1.13 mL, 6.48 mmol) were added to a THF solution (20 mL) of 4-hydroxy-2-hydroxymethyl) cyclopenta-2-en-1-one (415 mg, 3.24 mmol) at room temperature. After stirring the reaction solution at the same temperature for 24 hours, an aqueous solution of saturated ammonium chloride was added to stop the reaction. The mixture was separated using ethyl acetate (2×30 mL). The organic layer was washed with saturated brine and dried over anhydrous magnesium sulfate. The residue remaining after removal under reduced pressure was purified with silica gel chromatography (hexane/EtOAc 1:1). 4-Hydroxy-2-(triphenylmethyloxymethyl) cyclopenta-2-en-1-one (390 mg, 32%) was obtained as a pale yellow amorphous to viscous oily substance.

$^1$H NMR (400 Mz, CDCl$_3$): δ 1.85 (d, J=6.4 Hz, 1H), 2.30 (dd, J=2.0, 18.8 Hz, 1H), 2.80 (dd, J=6.0, 18.8 Hz, 1H), 3.93-3.94 (m, 2H), 4.98-5.02 (m, 1H), 7.22-7.45 (m, 15H), 7.61 (q, J=2.0 Hz, 1H) ppm; $^{13}$C NMR (101 Mz, CDCl$_3$) δ 45.2, 58.6, 68.8, 87.1, 127.2, 127.9, 128.5, 143.6, 145.8, 156.1, 204.5 ppm.

EXAMPLE 5

Manufacture of an Optically-Active Cyclopentenone

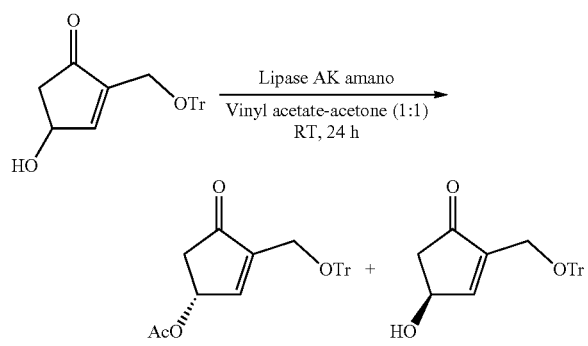

Lipase AK amano (81 mg) was added to vinyl acetate-acetone solution (1:1, 2.2 mL) of 4-hydroxy-2-(triphenylmethyloxymethyl) cyclopenta-2-en-1-one (81.7 mg, 0.22 mmol) at room temperature and stirred at the same temperature for 24 hours. The enzyme was removed by filtration, and the filtrate was distilled off under reduced pressure. The obtained residue was purified with silica gel chromatography (hexane/EtOAc=2:1). 4R-acetoxy-2-(triphenylmethyloxymethyl) cyclopenta-2-en-1-one ((R)-AC form) (32 mg, 36%), and 4S-hydroxy-2-(triphenylmethyloxymethyl) cyclopenta-2-en-1-one ((S)-monotrityl form) (40 mg, 49%) were obtained, respectively.

$^1$H NMR (400 Mz, CDCl$_3$): δ 2.13 (s, 3H), 2.36 (dd, J=2.0, 18.8 Hz), 2.86 (dd, J=6.0, 18.8 Hz, 1H), 3.92-3.93 (m, 2H), 5.81-5.84 (m, 1H), 7.22-7.44 (m, 15H) 7.63 (d, J=2.4, 1H) ppm; $^{13}$C NMR (101 Mz, CDCl$_3$) δ 20.9, 41.9, 58.7, 70 4, 87.1, 127.2, 127.9, 128.4, 143.4, 147.5, 152.0, 170.5, 203.1 ppm.

The invention claimed is:

1. A method for producing the compound of formula (3) or the compounds of formula (4), comprising reacting the compound of formula (2) with a carboxylic acid ester of an unsaturated alcohol in the presence of a hydrolase to give a mixture of the compounds of formula (3) and formula (4), wherein the mixture of the compounds of formula (3) and formula (4) is then separated to produce an optically-active compound of formula (3) or an optically active compound of formula (4), wherein R$^1$ is tert-butyldimethylsilyl or triphenylmethyl and R$^2$ is an acyl group

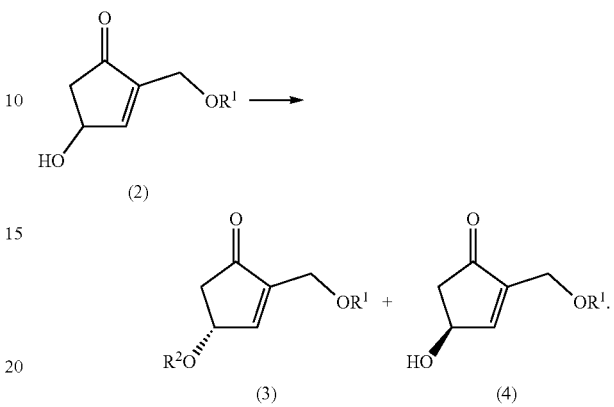

2. The method according to claim 1, wherein the carboxylic acid ester of an unsaturated alcohol is vinyl acetate, vinyl propionate, vinyl valerate, isopropenyl acetate, isopropenyl propionate, or isopropenyl valerate, and the hydrolase is lipase.

3. The method according to claim 1, wherein the carboxylic acid ester of an unsaturated alcohol is vinyl acetate, and the hydrolase is Amano Lipase PS or Amano Lipase AK.

4. A compound represented by formula (I) or an optically-active form thereof,

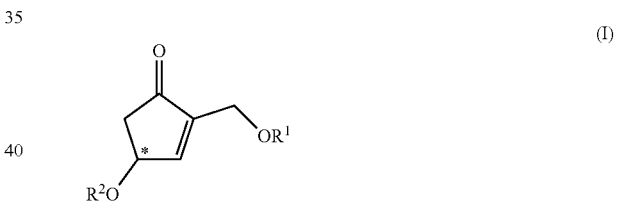

wherein,
R$^1$ is a tent-butyldimethylsilyl, and
R$^2$ is acetyl, propionyl, n-butyryl, iso-butyryl, n-valeryl or caproyl, and wherein the * represents an asymmetric carbon atom.

5. A compound represented by formula (I) or an optically-active form thereof,

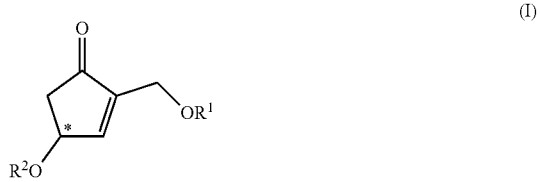

wherein,
R$^1$ is triphenylmethyl, and
R$^2$ is an acyl group, and
wherein the * represents an asymmetric carbon atom.

* * * * *